United States Patent [19]

Finley

[11] 4,263,906
[45] Apr. 28, 1981

[54] TWO PART WOUND BANDAGE

[76] Inventor: Michael S. Finley, 3407 Luckie Rd., Cheyenne, Wyo. 82001

[21] Appl. No.: 66,163

[22] Filed: Aug. 13, 1979

[51] Int. Cl.³ ............................................. A61F 13/00
[52] U.S. Cl. ..................................... 128/157; 128/171
[58] Field of Search ................... 128/157, 132 R, 165, 128/82, 155, 156, 171

[56] References Cited

U.S. PATENT DOCUMENTS

| | | | |
|---|---|---|---|
| 2,367,690 | 1/1945 | Purdy | 128/132 R |
| 2,663,020 | 12/1953 | Cushman | 128/132 R |
| 3,824,998 | 7/1974 | Snyder | 128/157 |

*Primary Examiner*—John D. Yasko
*Attorney, Agent, or Firm*—Hubbell, Cohen, Stiefel & Gross

[57] ABSTRACT

A wound bandage comprises a two-part bandage frame having an upper frame member and a separable lower frame member, with the upper frame member having a wound dressing attached thereto and being removably securable to the lower frame member to enable periodic changing of the dressing or inspection or treatment of the wound while the lower frame member remains affixed around the wound framing the area to be treated. The lower frame member may be held in place around the wound by sutures threaded through apertures in lobes on the lower frame member. This arrangement finds particular application in difficult to bandage wounds such as found on animals.

3 Claims, 6 Drawing Figures

U.S. Patent  Apr. 28, 1981  Sheet 1 of 2  4,263,906
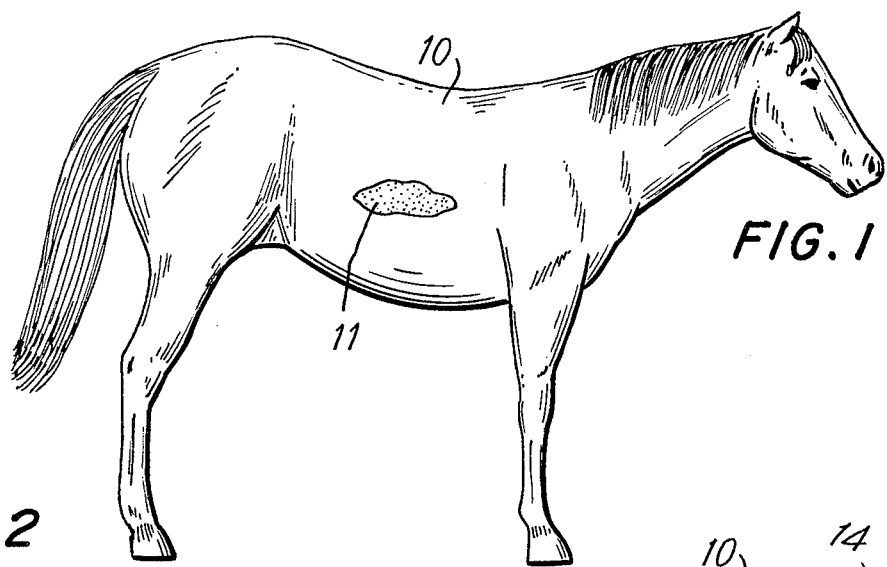
FIG. 1
FIG. 2
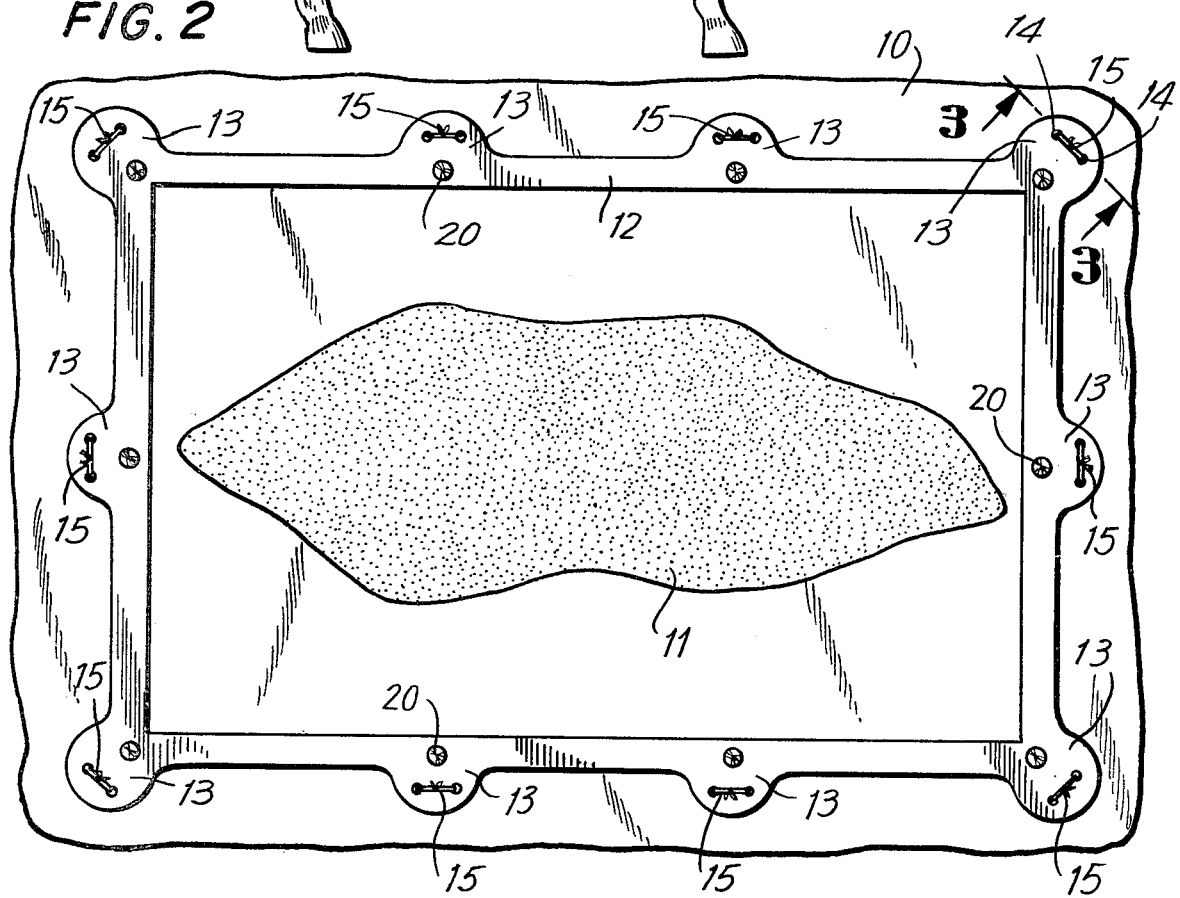
FIG. 3
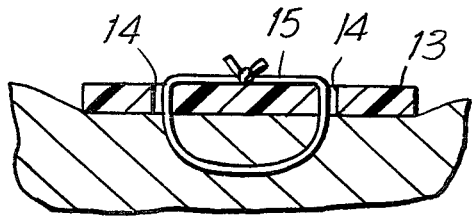
FIG. 6
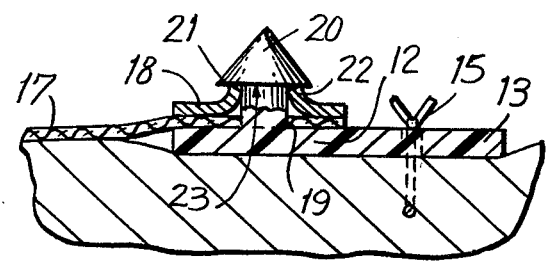

TWO PART WOUND BANDAGE

BACKGROUND OF THE INVENTION

1. Field of the Invention

This invention generally relates to bandages, and in particular, to bandages having a wound dressing portion which may be readily removed or changed.

2. Discussion of the Prior Art

The treatment of various types of bandaged wounds often requires either periodic access to the wound for inspection and supplemental treatment or periodic changing of whatever form of dressing or covering is applied thereto. Such access or changing in the past has usually required destruction of the entire bandage, thereby requiring a completely new bandage to be applied which can be both costly and time consuming depending upon the location and size of the wound to be bandaged. This problem is particularly acute with respect to animals which often have difficult to bandage areas or which try to remove bandages and especially larger animals which require large bandages.

A prior art bandage which purports to allow limited access to the bandaged area without requiring removal of the entire bandage is shown in U.S. Pat. No. 2,273,873. The prior art bandage disclosed therein is formed from strips of doublesided adhesive tape which is cut into strips and placed around the wound to be dressed by pressing one side against the skin. A dressing may then be placed over the encircled area and pressed against the other side of the adhesive strips for maintaining it in that position. In the event that periodic access is desired to the wounded area, the dressing portion must then be cut open. If this is done, then the cuts must be taped closed to recover the wound. As adhesive is not normally reusable, the changing of the dressing portion of this bandage requires either that the first adhesive strips used to attach the bandage to the wounded animal or person be removed and a new bandage be applied, or that additional double-sided adhesive strips be affixed over the initial strips with the new dressing then being applied thereto. This would result in a thickening of the bandage which would not lend itself to multiple changes. Thus, this form of bandage does not allow for any savings in cost or time in the process of changing the dressing or inspecting the wound.

Another type of prior art bandage known to applicant is shown in U.S. Pat. No. 4,026,290 which discloses a device for administering medicaments through the skin by the absorption process. The device, which appears to be reusable, is adapted to be strapped around the limb of an animal to hold a medicament in close contact with the skin thereof. The absorption of the medicament usually takes place over a period of time, such as weeks or months. Although this device is easily removed and reattached, no provision is made for attaching the medicant to the frame which must completely cover the medicant to hold it over the wounded area. Moreover, because of this, this device does not readily lend itself to the coverage of large wounds which must be periodically inspected or changed. These disadvantages of the prior art are overcome by the present invention.

SUMMARY OF THE INVENTION

A wound bandage constructed according to the present invention includes a first flexible frame, wound bandage mounting member surroundably affixable about a wound for framing the wound area to be treated, a wound dressing, a second flexible frame member affixed to the wound dressing for forming an integrated wound covering and means for removably attaching the second frame member to the affixed first frame member for enabling removable coverage of the wound with the wound dressing while the first frame member is affixed about the wound, whereby the dressing may be periodically changed and the wound may be periodically exposed to facilitate treatment or inspection thereof while the first frame remains affixed around the wound treatment area. Alternatively, the wound bandage of the present invention includes a flexible frame, wound bandage mounting member surroundably affixable about a wound for framing the wound area to be treated, a wound dressing, and a plurality of reusable clip means located on the flexible frame member for removably fastening said wound dressing to said flexible frame member for enabling removable coverage of the wound with the wound dressing while the frame member is affixed about the wound.

BRIEF DESCRIPTION OF THE DRAWINGS

The present invention is illustratively shown and described in reference to the appended drawings in which:

FIG. 1 is a side view of an animal having a wound to which the bandage of the present invention may be applied;

FIG. 2 is an enlarged view of the wound shown in FIG. 1 with a portion of a bandage constructed according to the present invention applied thereto;

FIG. 3 is a sectional view taken along view lines 3—3 in FIG. 2 and showing a means for attaching the bandage portion shown in FIG. 2 to a living body;

FIG. 6 is a sectional view taken along view lines 6—6 of FIG. 5 and showing a means for attaching the wound dressing of FIG. 4 to the bandage member shown in FIG. 2.

DETAILED DESCRIPTION OF THE DRAWINGS

Figure 4:
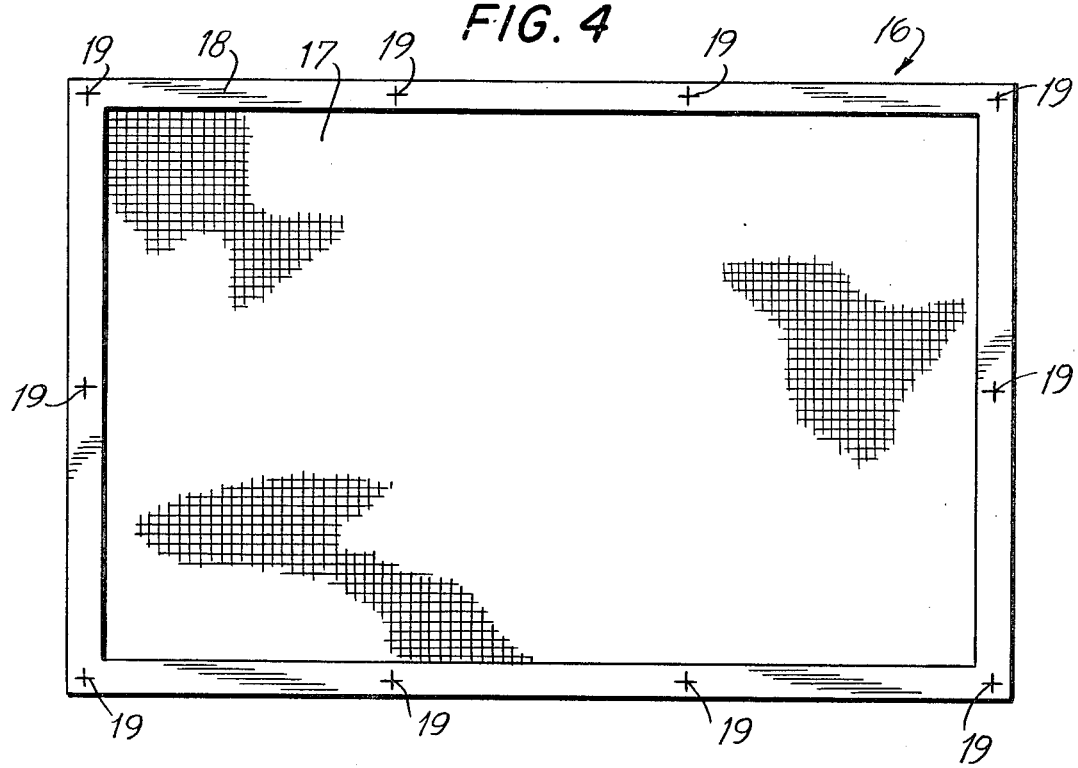
FIG. 4 is a top view of a wound dressing which may be used in conjunction with the bandage of FIG. 2.

Referring now to the drawings in detail, a horse 10 having a large wound 11 located on its side is shown by way of example. Such a wound is difficult to dress by virtue of the girth of the horse in the wound area. A bandage, wrapped around the horse in the same manner as a saddle would require a great deal of material and additional means for insuring that the bandage did not slip in a rotational or longitudinal manner on the horse 10.

FIG. 2 shows an enlargement of the wound 11 and the area of the horse located therearound. A flexible frame, wound bandage mounting member 12 is shown affixed to the horse 10 and surrounding the wound 11. The frame member 12 is flexible in order to allow it to conform to the curvature of the horse's body and to allow it to change shape in accordance with the animal's movements, thus preventing unnecessary stress from being placed on the points of attachment to the horse's body. The frame member 12 is shown in rectangular shape for purposes of illustration only and may be made in any convenient shape which allows it to be attached around a wound or wounded area. The frame member 12 is also illustrated in the form of a closed loop but may also be made in any suitable form such as a plurality of strips or a single strip which may be applied to substantially surround the wound.

The frame member 12 includes a plurality of lobes 13 by which the frame member 12 may be surroundably affixed about a wound for framing the wound area to be treated. The lobes 13, as shown in cross section in FIG. 3, include a pair of holes or apertures 14 through which the member 12 may be attached such as with a suture 15, as shown. Of course any other suitable form of attachment may be used for affixing the frame member 12 around the wounded area, such as skin staples or a suitable adhesive means. Generally, the lobes 13 are evenly spaced along the frame member 12 in order to evenly distribute the attachment points of the bandage to the animal. Also, the frame member 12 may be made from any suitable material which exhibits flexibility and which preferably does not react with living tissue. The preferred flexibility of the frame member 12 allows the bandage to conform to the required shape of each individual application and in cases where movement is involved, the flexibility allows the bandage to follow the movement of the body to which it is attached without placing undue strain on the attachment points, i.e., sutures 15.

A wound dressing 16, suitable for use with the frame member 12, is shown in FIG. 4. The wound dressing 16 has a rectangular shape which preferably conforms to that of the frame member 12 but may, alternatively, be formed in any shape which is suitable for use with the frame member for which it is intended. The wound dressing 16 includes a dressing portion 17 intended for covering the wound area to be treated. The dressing portion 17 may be made of any suitable dressing material including any of the special non-stick dressing materials such as those currently available under the trademarks Telfa from Kendall Industries and Dermicel from Johnson & Johnson. A second flexible frame 18 is shown preferably attached to the periphery or marginal portion of the dressing 16 for forming an integrated wound dressing 16. The second frame member 18 like the first frame member 12 is preferably flexible in order to allow the bandage to conform to the shape of the animal and change shape in conformation with movements of the animal to prevent undue strain from being placed upon the points of attachment both to the frame member 12 and to the animal's body. The second flexible frame member 18 preferably includes a plurality of perforations 19 by which the flexible frame member 18 may be attached to the frame member 12 by suitable means as described below. The frame member 18 may be attached to the marginal portion of the dressing 16 by any suitable means such as adhesive or the like. Preferably flexible frame member 18 provides then integrated dressing 16 with strength along its marginal portions and thus insures secure attachment of the dressing 16 to the other or base frame member 12. Thus, as shown and preferred on FIGS. 4-6, frame member 18 is capable of maintaining some amount of closure between it and the base frame member 12, between the various points of connection.

Figure 5:
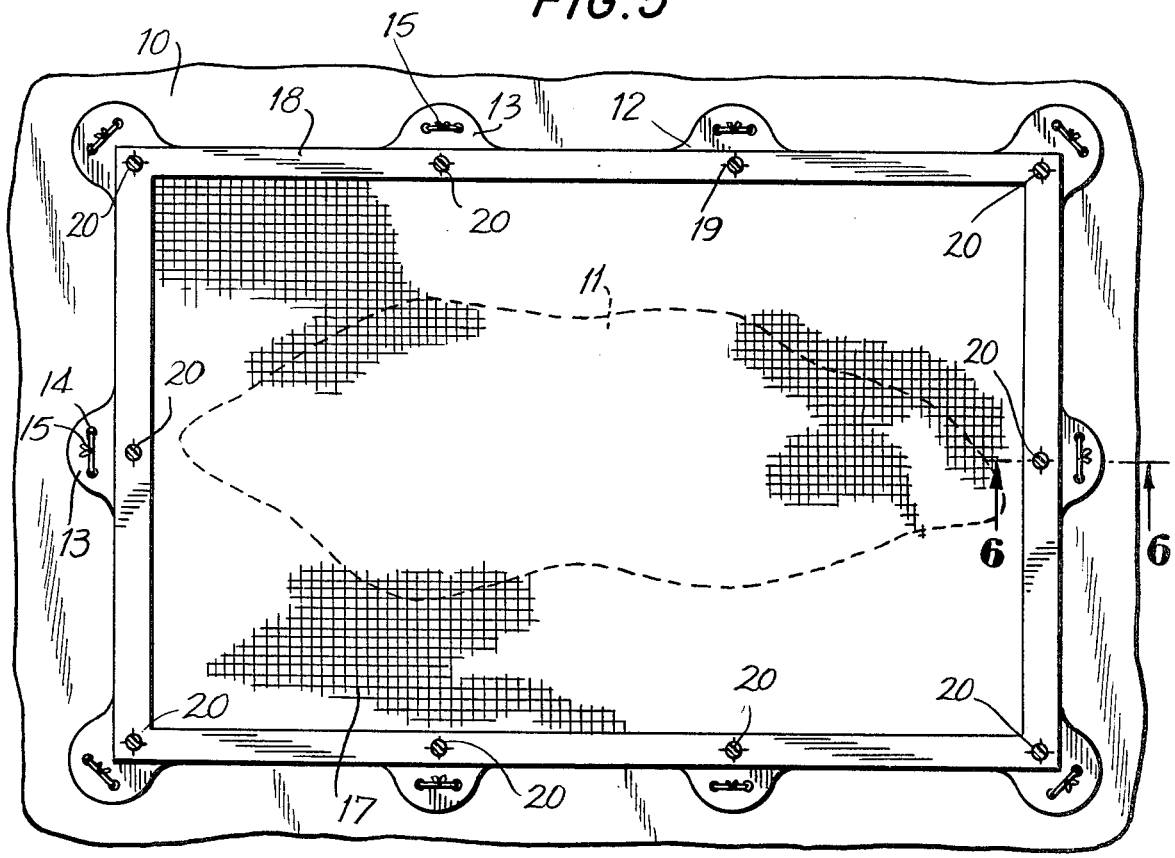
FIG. 5 shows the wound dressing of FIG. 4 used in conjunction with the wound and bandage of FIG. 2.

The interconnection between the wound dressing 16 and the frame member 12 is best illustrated with reference to FIGS. 5 and 6 in which the two elements of the bandage are shown in place over the wound 11. As also shown and preferred in FIG. 2, and as shown in detail in the cross sectional view of FIG. 6, the base frame member 12 includes a plurality of clip means 20 for removably attaching the wound dressing 16 or the second frame member 18 to the frame member 12 for enabling removable coverage of the wound, with the wound dressing, while the first frame member 12 is affixed about the wound 11. In one form of the present invention the clip means 20 are reusable for allowing the dressing 16 to be periodically changed and the wound 11 to be periodically exposed to facilitate treatment or inspection thereof while the frame member 12 remains affixed around the wound treatment area. The clip means 20 may be constructed in any suitable form which allows a relatively unlimited number of wound dressing changes without causing substantial deterioration of the clip means 20 attachment function. In one presently preferred form, illustrated on FIGS. 4-6, the clip means 20 are bayonet-like fasteners adapted for penetrating corresponding apertures or slits 19 in flexible frame member 18. In this form, the clip means 20 each includes a flange 21 protruding therefrom to retain each clip or fastener 20 in its corresponding aperture 19 in the overlying frame member 18. As shown in FIG. 6, penetration of a slit or aperture 19 by an end of the fastener 20 resiliently deforms the sides 22 of the aperture 19 causing them to pass over the flange 21. The downward facing surface 23 of the flange 21 is then capable of exerting force on the deformed edge 22 or simply the sides of the aperture 19 in order to retain the overlying flexible frame member 18 affixed to the base flexible frame member 12. Upon removal of the wound dressing 16, the clip means or fasteners 20 by which the wound dressing 16 is connected to the flexible frame 12 remain intact and may be reused with subsequent dressings while the base flexible frame member 12 remains attached to the animal or the body being treated framing the area of treatment. Thus, the entire bandage is not destroyed when the dressing 16 is changed or access to the wound is required and the delicate bandage-animal interface can remain intact. Alternatively, various other forms of clip means 20 may be used to secure the wound dressing 16 to the frame means 12, such as Velcro strips, which would not require deformation of the overlying frame member 18 to obtain a secure attachment.

Thus, a bandage constructed according to the present invention exhibits a number of important advantages over prior art bandages such as enabling the dressing portion 17 of the bandage to be easily changed or opened for inspection of the wound without interfering with the bandage/body interface. When the bandage of the present invention is changed, the only portion which is replaced is the dressing 16, thus reducing bandage costs and labor time, especially when frequent changes are required. In addition, when the bandage is applied to large or hard to bandage areas, much time is saved in the changing of the dressing because the entire bandage need not be removed and replaced with each changing, with the treatment area remaining defined by the base frame held in place throughout the treatment period. This advantage is important in hospitals where it can save nurses' time and avoid potential error in reapplying a new dressing to the wrong area. The present invention also eases the discomfort of animals or human patients inherent in the changing of the bandage/body interface, i.e., such as the removal of adhesive tape from the skin each time the bandage is changed. In animal applications, the bandage of the present invention is especially useful. As the attachment of the bandage to the animal need not be changed just to change the dressing, that attachment may be of a more permanent and secure nature such as suturing instead of adhesive. Thanks to the more permanent attachment, an animal will be less likely to remove the bandage or displace it through movement. Also, with respect to large animals, a bandage such as that of the present invention, which can be localized to the injured area and does not require a wrapping around the animal, will be more comfortable for the animal and save a great deal in material costs. Also such a localized or smaller bandage is less likely to be either accidentally or purposely interfered with by the animal.

It is to be understood that the above-described embodiments of the present invention are to be taken as illustrative and not in a limiting sense and that various modifications may be made to the embodiments without departing from the scope of the invention as defined in the appended claims.

What is claimed is:

1. A flexible multi-component wound bandage comprising:

a first flexible base frame wound bandage mounting member surroundably affixable about a wound for defining a bandage/body interface by framing the wound area to be treated;

a flexible porous wound dressing having marginal portions;

a second flexible top frame member affixed to said marginal portions of said wound dressing for strengthening said wound dressing along said marginal portions while enabling secure attachment of said would dressing to said first flexible base frame member at said bandage/body interface; and reusable clip means disposed on said first flexible base frame member for removably attaching said second frame member to said first frame member at said defined bandage/body interface for enabling removable flexible coverage of said wound with said flexible porous wound dressing, said reusable clip means including a plurality of spaced apart bayonet-like fasteners, said second frame member having a plurality of spaced apart apertures corresponding to said bayonet-like fasteners for penetration thereby, each of said fasteners including a penetrating end for penetrating said second frame corresponding aperture and a flange protruding therefrom to retain said fastener in said corresponding second frame aperture after penetration thereof for maintaining removable flexible closure between said first and second flexible frame members, whereby said flexible multi-component wound bandage may provide a flexible bandage/body interface for covering said wound and said dressing may be periodically changed and said wound may be periodically exposed to facilitate treatment or inspection thereof while said bandage/body interface remains intact.

2. The bandage of claim 1, wherein said first frame member includes a plurality of lobes having apertures therethrough for enabling suturing of said first frame member to the area adjacent said wound treatment area to affix said first frame member around said wound treatment area.

3. The bandage of claim 1, wherein said first frame member is in the shape of a closed loop for circumscribing said wound when affixed therearound.

* * * * *